(12) United States Patent
Ji et al.

(10) Patent No.: US 12,428,620 B2
(45) Date of Patent: Sep. 30, 2025

(54) **STRAIN OF *LACTOBACILLUS SAKEI* HEM224, AND COMPOSITION FOR TREATING INFLAMMATION OR ASTHMA COMPRISING STRAIN OR CULTURED PRODUCT THEREOF**

(71) Applicant: HEM PHARMA INC., Pohang-si (KR)

(72) Inventors: Yo Sep Ji, Suwon-si (KR); So Young Park, Suwon-si (KR)

(73) Assignee: HEM PHARMA INC., Pohang-si (KR)

( * ) Notice: Subject to any disclaimer, the term of this patent is extended or adjusted under 35 U.S.C. 154(b) by 446 days.

(21) Appl. No.: 17/760,112

(22) PCT Filed: Dec. 30, 2020

(86) PCT No.: PCT/KR2020/019432
§ 371 (c)(1),
(2) Date: Aug. 4, 2022

(87) PCT Pub. No.: WO2021/157867
PCT Pub. Date: Aug. 12, 2021

(65) Prior Publication Data
US 2023/0025456 A1 Jan. 26, 2023

(30) Foreign Application Priority Data
Feb. 5, 2020 (KR) .................. 10-2020-0013674

(51) Int. Cl.
*C12N 1/20* (2006.01)
*A23L 33/135* (2016.01)
(Continued)

(52) U.S. Cl.
CPC ............. *C12N 1/20* (2013.01); *A23L 33/135* (2016.08); *A61K 35/747* (2013.01); *A61P 11/06* (2018.01);
(Continued)

(58) Field of Classification Search
None
See application file for complete search history.

(56) References Cited

U.S. PATENT DOCUMENTS

2004/0147010 A1  7/2004  Vidal et al.
2018/0064766 A1  3/2018  Rhee et al.

FOREIGN PATENT DOCUMENTS

JP  2013193996     9/2013
KR  20120100608 A  9/2012
(Continued)

OTHER PUBLICATIONS

Kim et al. Multifunctional effects of Lactobacillus sakei HEM 224 on the gastrointestinal tract and airway inflammation, Scientific Reports vol. 13, Article No. 17918 (2023) (Year: 2023).*

(Continued)

*Primary Examiner* — Louise W Humphrey
*Assistant Examiner* — Alexander M Duryee
(74) *Attorney, Agent, or Firm* — NKL Law; Jae Youn Kim

(57) ABSTRACT

The present disclosure relates to a strain of *Lactobacillus sakei* HEM224 (KCTC14065BP) and a composition for treating, preventing or alleviating inflammation or asthma, comprising the strain. A strain of *Lactobacillus sakei* HEM224 (KCTC14065BP) according to an embodiment of the present disclosure inhibits the production of pro-inflammatory factors, and exhibits an effect of treating asthma in an asthma animal model. Therefore, the strain can be applied to pharmaceutical compositions, food compositions, health functional food compositions and feed compositions for treating, preventing or alleviating inflammation or asthma.

4 Claims, 7 Drawing Sheets

(51) Int. Cl.
    *A61K 35/747*     (2015.01)
    *A61P 11/06*     (2006.01)
    *A61P 29/00*     (2006.01)
    *C12R 1/225*     (2006.01)

(52) U.S. Cl.
    CPC ........... *A61P 29/00* (2018.01); *A23V 2002/00* (2013.01); *A23V 2400/179* (2023.08); *C12R 2001/225* (2021.05)

(56) References Cited

FOREIGN PATENT DOCUMENTS

| KR | 101678317 B1 | 11/2016 |
| KR | 101731903 B1 | 5/2017 |
| KR | 20180036592 A | 4/2018 |
| KR | 20190133640 A | 12/2019 |
| WO | 2013155370 A1 | 10/2013 |

OTHER PUBLICATIONS

International Search Report issued in PCT/KR2020/019432, dated Apr. 5, 2021.
European Search Report for European Application No. 20917302.0, dated Mar. 14, 2024.
Min Sung Kwon et al., "Lactobacillus sakei WIKIM30 Ameliorates Atopic Dermatitis-Like Skin Lesions by Inducing Regulatory T Cells and Altering Gut Microbiota Structure in Mice. Mice", Frontiers in Immunology , vol. 9, Aug. 14, 2018, pp. 1-11.

\* cited by examiner

STRAIN OF *LACTOBACILLUS SAKEI* HEM224, AND COMPOSITION FOR TREATING INFLAMMATION OR ASTHMA COMPRISING STRAIN OR CULTURED PRODUCT THEREOF

TECHNICAL FIELD

The present disclosure relates to a strain of *Lactobacillus sakei* HEM224 (KCTC14065BP) and a composition for treating, preventing, or alleviating lung inflammation or asthma, comprising the strain.

BACKGROUND

Bronchial asthma is a chronic disease which requires lifelong treatment once symptoms develop and is a huge burden on the public health system. Unlike other chronic diseases such as hypertension or diabetes which occur in middle-aged or older adults, bronchial asthma is a disease that occurs in all age groups, from children to the elderly. The prevalence of allergic asthma continues to increase due to changes in the living environment caused by rapid industrialization, and the asthma-related economic burden is reaching almost 2 trillion KRW (USD 2 billion). Also, it is reported that as the temperature and carbon dioxide level increases due to global warming, plants which can trigger allergic reaction to humans are diversifying, and the risk of pollen-induced allergy and asthma increases.

Allergic asthma is a disease in which breathing difficulties occur due to bronchial constriction and hypersecretion of mucus caused by bronchial hyperresponsiveness to an allergen. Particularly, the hypersecretion of mucus is known to be caused by allergens such as house dust mites or pollen in the respiratory tract. When an allergen invades into the airways, the immune system detects it and produces Immunoglobulin E (IgE). IgE acts as a receptor for mast cells in the bronchia, and when the allergen invades again, the mast cells respond to the allergen and secrete various signaling molecules such as histamine that trigger inflammatory response in the respiratory tract. Then, the mucous membrane becomes to be inflamed and mucus is excessively secreted, which increases airway resistance and causes breathing difficulties such as overinflation of the lungs. When allergic asthma is triggered, normal airway cells such as fibroblasts, myofibroblasts, epithelial cells and smooth muscle cells produce cytokines and growth factors associated with chronic airway inflammation.

As the cause of allergic asthma is unclear, environmental therapy, drug therapy using bronchodilators and anti-inflammatory agents to treat allergic inflammation and immunotherapy to improve allergic constitution have been tried. However, although various compositions for treating asthma have been developed (Korean Patent No. 10-1731903), finding effective treatment is difficult because allergic asthma is chronic and recurrent disease.

Under these circumstances, the present inventors have made extensive efforts to develop an excellent composition which is capable of suppressing airway inflammatory response and treating and/or alleviating asthma. As a result, the present inventors developed a novel strain that can promote the production of anti-inflammatory factors while suppressing the production of factors that induce asthma or factors that induce an inflammatory response.

DISCLOSURE OF THE INVENTION

Problems to be Solved by the Invention

The present disclosure is to provide a strain of *Lactobacillus sakei* HEM224 (KCTC14065BP) and a composition for treating, preventing, or alleviating inflammation or asthma, comprising the strain.

However, problems to be solved by the present disclosure are not limited to the above-described problems. Although not described herein, other problems to be solved by the present disclosure can be clearly understood by a person with ordinary skill in the art from the following description.

Means for Solving the Problems

A first aspect of the present disclosure provides a strain of *Lactobacillus sakei* HEM224 (KCTC14065BP).

A second aspect of the present disclosure provides a food composition for alleviating and/or preventing inflammation or asthma, comprising a strain of *Lactobacillus sakei* HEM224 (KCTC14065BP) or a cultured product thereof as an active ingredient.

A third aspect of the present disclosure provides a pharmaceutical composition for treating and/or preventing inflammation or asthma, comprising a strain of *Lactobacillus sakei* HEM224 (KCTC14065BP) or a cultured product thereof as an active ingredient.

Effects of the Invention

According to an embodiment of the present disclosure, a strain of *Lactobacillus sakei* HEM224 (KCTC14065BP) suppresses the production of pro-inflammatory factors, and exhibits an effect of treating asthma in an animal asthma model. Therefore, the strain can be applied to pharmaceutical compositions, food compositions, health functional food compositions, feed compositions and for treating, preventing, or alleviating inflammation or asthma.

BEST MODE FOR CARRYING OUT THE INVENTION

Figure 1:
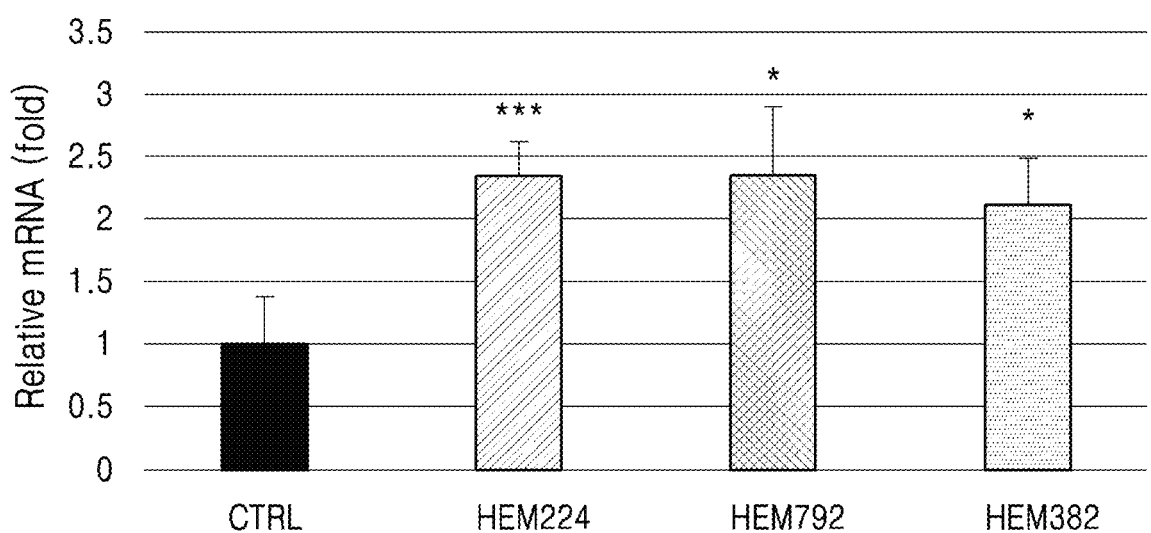
FIG. 1 is a diagram confirming that a novel strain of the present disclosure has an effect of promoting the production of interleukin 10 (IL-10).

Hereinafter, embodiments of the present disclosure will be described in detail with reference to the accompanying drawings so that the present disclosure may be readily implemented by a person with ordinary skill in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the other element and a case that any other element exists between these two elements.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Hereinafter, embodiments and examples of the present disclosure will be described in detail with reference to the accompanying drawings. However, the present disclosure may not be limited to the following embodiments, examples, and drawings.

A first aspect of the present disclosure provides a strain of *Lactobacillus sakei* HEM224 (KCTC14065BP).

In an embodiment of the present disclosure, the strain may modulate the production, expression, and activation of pro-inflammatory or inflammatory factors. Specifically, the pro-inflammatory or inflammatory factors may include at least one selected from the following group consisting of pro-inflammatory or inflammatory cytokines, but are not limited thereto: IL-4, IL-5, IL-3, IL-6, IL-7, IL-8, IL-9, IL-12, IL-13, IL-14, IL-17A, IL-33 and IgE.

In an embodiment of the present disclosure, the strain may promote the production, expression, and activation of anti-inflammatory factors. Specifically, the anti-inflammatory factors may be cytokines, such as IL-10 or TGF-$\beta$, but are not limited thereto.

In an embodiment of the present disclosure, the strain may modulate inflammatory or immune response. Specifically, the strain may have an anti-inflammatory function.

Through the whole document, the term "anti-inflammation" refers to suppressing an inflammatory response, and specifically, alleviation of an inflammatory disease that may be caused by an inflammatory trigger, reduction of symptoms, treatment, suppression or delayed onset of the disease, or the like.

Through the whole document, the term "inflammatory disease" may be defined as a pathological symptom caused by an inflammatory response specified by a local or systemic defensive response to autoimmunity or infection of any external infectious source such as external physical and chemical irritation, bacteria, fungi, viruses, and various allergens. Such an inflammatory response involves a series of complex physiological reactions including activation of various inflammatory mediators and enzymes associated with immune cells (e.g., iNOS, COX-2, etc.), secretion of inflammatory mediators (e.g., secretion of NO, TNF-$\alpha$, IL-6, interleukins, etc.), body fluid retention, cell migration, tissue destruction, etc., and may be manifested externally by symptoms including erythema, pain, edema, fever and deterioration or loss of specific functions of the body. Since the inflammatory disease could be acute, chronic, ulcerative, allergic or necrotic, as long as any disease is included in the definition of inflammatory disease, it does not differentiate whether the disease is acute, chronic, ulcerative, allergic or necrotic. Specifically, the inflammatory disease may include asthma, allergic and non-allergic rhinitis, chronic and acute rhinitis, chronic and acute gastritis or enteritis, ulcerative gastritis, acute and chronic nephritis, acute and chronic hepatitis, chronic obstructive pulmonary disease, pulmonary fibroma, irritable bowel syndrome, inflammatory pain, migraine, headache, back pain, fibromyalgia, myofascial disease, viral infection (e.g., hepatitis C), bacterial infection, fungal infection, burns, surgical or dental wounds, hyper-prostaglandin E syndrome, atherosclerosis, gout, arthritis, rheumatoid arthritis, ankylosing spondylitis, Hodgkin's disease, pancreatitis, conjunctivitis, iritis, scleritis, uveitis, dermatitis (including atopic dermatitis), eczema, multiple sclerosis and the like.

In an embodiment of the present disclosure, the strain may be capable of treating, alleviating, reducing and/or preventing an inflammatory disease, and specifically, the inflammatory disease may include at least one selected from the group consisting of asthma, allergic and non-allergic rhinitis, chronic and acute rhinitis, dermatitis, atopic dermatitis and sinusitis, but is not limited thereto.

In an embodiment of the present disclosure, the strain may function to treat, prevent, alleviate, or reduce asthma.

In an embodiment of the present disclosure, the strain may have an anti-inflammatory effect or may treat or prevent an inflammatory disease or asthma. Specifically, the strain may be contained in various compositions such as pharmaceutical compositions, food compositions, health functional food compositions, feed compositions, cosmetic compositions, skin external compositions and the like for treating, preventing, or alleviating inflammation or asthma.

A second aspect of the present disclosure provides a food composition for alleviating or preventing inflammation or asthma, comprising a strain of *Lactobacillus sakei* HEM224 (KCTC14065BP) or a cultured product thereof as an active ingredient. The features described above in respect of the first aspect of the present disclosure may equally apply to the food composition according to the second aspect of the present disclosure.

Through the whole document, the term "alleviate" refers to all activities causing an anti-inflammatory effect or reducing or improving inflammation, inflammatory diseases or asthma symptoms by administering the composition.

In an embodiment of the present disclosure, the composition may inhibit the production, expression, or activation of pro-inflammatory or inflammatory factors or promote the production, expression, or activation of anti-inflammatory factors. Specifically, the composition may be an anti-inflammatory composition.

In an embodiment of the present disclosure, the composition may contain a strain of *Lactobacillus sakei* HEM224, live cells, heat-killed cells, culture fluid, fragments and/or extracts thereof.

Through the whole document, the term "heat-killed bacteria" is opposite to the term "live bacteria" and refers to bacterial cell bodies obtained by suppressing the growth of bacteria such as heat-treating to live bacteria and metabolites thereof obtained by fermentation. The heat-killed bacteria may contain cytoplasm, cell wall, antibacterial substances such as bacteriocin, polysaccharides, organic acid, and the like. Products using the heat-killed bacteria have higher stability than live bacteria products and are particularly excellent in heat resistance. Therefore, the products using the heat-killed bacteria are easier to store and have longer shelf life than the live bacteria products. Furthermore, since the regulations on the use of antibiotics become stricter, there are only a handful of companies that have produced heat-killed bacteria products. Therefore, considering the application as substitutes and the number of the producing companies, the marketability and growth potential is very high.

Through the whole document, the term "culture fluid" refers to a substance obtained by culturing the strain of the present disclosure in a known liquid medium or solid medium and may be interchangeably used with "cultured product".

Through the whole document, the term "food" may include meats, sausages, breads, chocolates, candies, snacks, cookies, pizza, ramens, other noodles, gums, dairy products including ice cream, soups, beverages, teas, drinks, alcohol drinks, vitamin complexes, health functional foods and health foods, and may include all foods in the accepted meaning.

Through the whole document, the term "health functional food" refers to foods prepared and processed using raw materials or ingredients having useful functions to the human body in accordance with the Health Functional Food Act, No. 6727, and the "functionality" refers to adjusting nutrients on a structure and a function of the human body or obtaining a useful effect for health such as a physiological action.

The food of the present disclosure can be manufactured by conventional methods used in the art, and can be manufactured by adding conventional raw materials and ingredients used in the art. Further, a formulation of the food is not limited as long as the formulation is accepted as a food. The food composition of the present disclosure may be prepared in a variety of formulations. Since the food is used as raw materials, unlike general drugs, the food composition is free from side effects which may occur when a drug is taken for a long time, and may have excellent portability. Therefore, the food of the present disclosure may be taken as a supplement for enhancing the effects of improving the intestinal environment.

The health food refers to a food having effects of actively maintaining or promoting health conditions, as compared with general foods, and a health supplement food refers to a food for supplementing health. If necessary, the health functional food, health food and health supplement food may be interchangeably used with each other. Specifically, the health functional food is a food prepared by adding *Lactobacillus sakei* HEM224 of the present disclosure to food materials such as beverages, teas, spices, gums, confectionery, etc., or prepared in a capsule, a powder or a suspension form. The health functional food means that it has a specific effect on health when consumed, but unlike general drugs, the health functional food is free from side effects that may occur when a drug is taken for a long time since the food is used as raw materials.

Since the food composition of the present disclosure can be routinely ingested, the food composition is expected to show a high efficacy on the improvement of intestinal environment and thus can be very usefully applied.

The food composition may further contain a physiologically acceptable carrier. The kind of the carrier is not particularly limited. Any carrier may be used as long as it is commonly used in the art.

Further, the food composition may further contain additional ingredients that are commonly used in food compositions to improve smell, taste, visuality, etc. For example, the food composition may contain vitamins A, C, D, E, B1, B2, B6, B12, niacin, biotin, folate, pantothenic acid, etc. Furthermore, the food composition may also contain minerals such as zinc (Zn), iron (Fe), calcium (Ca), chromium (Cr), magnesium (Mg), manganese (Mn), copper (Cu), chromium (Cr), etc. Moreover, the food composition may also contain amino acids such as lysine, tryptophane, cysteine, valine, etc.

Further, the food composition may also contain food additives, such as preservatives (potassium sorbate, sodium benzoate, salicylic acid, sodium dehydroacetate, etc.), disinfectants (bleaching powder, higher bleaching powder, sodium hypochlorite, etc.), antioxidants (butylhydroxyanisole (BHA), butylhydroxytoluene (BHT), etc.), colorants (tar color, etc.), color-developing agents (sodium nitrite, etc.), bleaching agents (sodium sulfite), seasonings (monosodium glutamate (MSG), etc.), sweeteners (dulcin, cyclamate, saccharin, sodium, etc.), flavors (vanillin, lactones, etc.), swelling agents (alum, potassium D-bitartrate, etc.), fortifiers, emulsifiers, thickeners (adhesive pastes), film-forming agents, gum base agents, antifoaming agents, solvents, improvers, etc. The additives may be selected and used in an appropriate amount depending on the type of food.

*Lactobacillus sakei* HEM224 of the present disclosure may be added as it is, or may be used in conjunction with other foods or food ingredients, and may be appropriately used according to a conventional method. The mixing amount of active ingredients may be appropriately determined depending on the purpose of use (prophylactic, health, or therapeutic treatment). In general, when a food or a beverage is manufactured, the food composition of the present disclosure may be added in an amount of 50 parts by weight or less, specifically 20 parts by weight or less based on the total weight of the food or the beverage. However, when taken for the purpose of health and/or hygiene, the food composition may be contained in an amount below the range. In addition, since there is no safety problem, the active ingredients may be used in an amount above the range.

The food composition of the present disclosure may be used as, for example, a health beverage composition, and in this case, the health beverage composition may further contain various flavors or natural carbohydrates, as in common beverages. The natural carbohydrates may include monosaccharides such as glucose and fructose; disaccharides such as maltose and sucrose; polysaccharides such as dextrin and cyclodextrin; and sugar alcohols such as xylitol, sorbitol and erythritol. The sweeteners may be natural sweeteners such as thaumatin or a stevia extract; or synthetic sweeteners such as saccharin or aspartame. The natural carbohydrate may be generally used in an amount of from about 0.01 g to about 0.04 g, and specifically, from about 0.02 g to about 0.03 g based on 100 mL of the health beverage composition of the present disclosure.

In addition, the health beverage composition may contain various nutrients, vitamins, minerals, flavors, colorants, pectic acid and salts thereof, alginic acid and salts thereof, organic acid, protective colloidal thickeners, pH regulators, stabilizers, antiseptics, glycerin, alcohols, or carbonating agents. Moreover, the health beverage composition may contain fruit flesh used to prepare natural fruit juices, fruit juice beverages or vegetable beverages. These ingredients may be used individually or in combination. A proportion of the additives is not critical, but is generally selected from 0.01 part by weight to 0.1 part by weight per 100 parts by weight of the health beverage composition of the present disclosure.

The food composition of the present disclosure may contain *Lactobacillus sakei* HEM224 of the present disclosure in a variety of % by weight as long as it can exhibit the effect of alleviating or preventing inflammation or asthma. Specifically, *Lactobacillus sakei* HEM224 of the present disclosure may be contained in an amount of 0.00001% by weight to 100% by weight or 0.01% by weight to 80% by weight based on the total weight of the food composition, but is not limited thereto.

In an embodiment of the present disclosure, the food composition may be a health functional food composition.

A third aspect of the present disclosure provides a pharmaceutical composition for treating or preventing inflammation or asthma, comprising a strain of *Lactobacillus sakei* HEM224 (KCTC14065BP) or a cultured product thereof as an active ingredient. The features described above in respect of the first and second aspects of the present disclosure may equally apply to the pharmaceutical composition according to the third aspect of the present disclosure.

In an embodiment of the present disclosure, the composition may contain a strain of *Lactobacillus sakei* HEM224, live bacterial cell bodies, heat-killed bodies, culture fluid, fragments and/or extracts thereof.

Through the whole document, the term "treat" refers to all activities reducing or alleviating symptoms of a disease by administering a pharmaceutical composition containing *Lactobacillus sakei* HEM224 of the present disclosure as an active ingredient to a subject with inflammation, an inflammatory disease or asthma.

In an embodiment of the present disclosure, the composition may inhibit the production, expression, or activation of pro-inflammatory or inflammatory factors or promote the production, expression, or activation of anti-inflammatory factors. Specifically, the composition may be an anti-inflammatory composition.

In an embodiment of the present disclosure, the pharmaceutical composition may be formulated and used as formulations for oral administration such as powders, granules, tablets, capsules, suspensions, emulsions, syrups or aerosol, external preparations, suppositories or sterile injection solutions by conventional methods, respectively, but is not limited thereto.

In an embodiment of the present disclosure, the pharmaceutical composition may be formulated with generally used diluents or excipients such as fillers, bulking agents, binders, wetting agents, disintegrating agents or surfactants, but is not limited thereto.

In an embodiment of the present disclosure, solid formulations for oral administration may include tablets, pills, powders, granules or capsules, and these solid formulations may be prepared by mixing heat-killed bodies of the strain with at least one of excipients such as starch, calcium carbonate, sucrose, lactose or gelatin. Except for the simple excipients, lubricants such as magnesium stearate or talc may be used, but the present disclosure may not be limited thereto.

In an embodiment of the present disclosure, liquid formulations for oral administration may include suspensions, solutions for internal use, emulsions and syrups, and may contain various excipients such as wetting agents, sweeteners, aromatics and preservatives in addition to generally used simple diluents such as water and liquid paraffin, but are not limited thereto.

In an embodiment of the present disclosure, formulations for parenteral administration may include sterilized aqueous solutions, water-insoluble excipients, suspensions, emulsions, lyophilized preparations and suppositories, but are not limited thereto. For example, the water insoluble excipients or suspensions may contain propylene glycol, polyethylene glycol, vegetable oil such as olive oil, injectable ester such as ethylolate, and the like, but are not limited thereto. For example, the suppositories may contain witepsol, macrogol, tween 61, cacao butter, laurin butter, glycerol, gelatin, and the like, but are not limited thereto.

The pharmaceutical composition according to an embodiment of the present disclosure may be a drug composition or a quasi-drug composition.

Through the whole document, the term "quasi-drug" refers to an article having a milder action than drugs, among articles being used for the purpose of diagnosis, treatment, improvement, alleviation, handling or prevention of human or animal diseases. For example, according to the Pharmaceutical Affairs Law, the quasi-drugs are those, excluding articles used as drugs, including articles used for the purpose of treating or preventing human or animal diseases and articles which have a mild action on or have no direct influence on the human body.

The quasi-drug composition of the present disclosure may be manufactured in a formulation selected from the group consisting of body cleanser, sanitizer, detergent, kitchen cleanser, detergent for cleaning, toothpaste, mouthwash, wet wipe, cleanser, soap, hand soap, hair cleanser, hair softener, humidifying filler, mask, ointment or filter filler, but is not limited thereto.

In an embodiment of the present disclosure, the pharmaceutical composition may be administered in a pharmaceutically effective amount. Through the whole document, the term "pharmaceutically effective amount" refers to an amount sufficient to treat or prevent diseases at a reasonable benefit/risk ratio applicable to any medical treatment or prevention. An effective dosage level may be determined depending on factors including severity of the disease, drug activity, a patient's age, body weight, health conditions, gender, sensitivity to the drug, administration time, administration route, and excretion rate of the composition of the present disclosure, duration of treatment, drugs blended with or co-administered with the composition of the present disclosure, and other factors known in the medical field. The pharmaceutical composition of the present disclosure may be administered individually or in combination with an ingredient known for treating intestinal diseases. It is important to administer an amount to obtain a maximum effect in a minimum amount without side effects by considering all of the above-described factors.

In an embodiment of the present disclosure, an administration dose of the pharmaceutical composition may be determined by a person with ordinary skill in the art in view of purpose of use, severity of the disease, a patient's age, body weight, gender, medical history or the kind of a material used as an active ingredient. For example, the pharmaceutical composition of the present disclosure may be administered at a dose of from about 0.1 ng/kg to about 1,000 mg/kg, and preferably, from about 1 ng/kg to about 100 mg/kg per adult, and the administration frequency of the composition of the present disclosure is not particularly limited, but the composition may be administered once a day or several times a day in divided doses. The administration dose or the administration frequency does not limit the scope of the present disclosure in any aspect.

A fourth aspect of the present disclosure provides a method for treating inflammation, an inflammatory disease or asthma, comprising administering the pharmaceutical composition of the present disclosure to a subject suffering from inflammation, an inflammatory disease or asthma in a pharmaceutically effective amount. The features described above in respect of the first to third aspects of the present disclosure may equally apply to the method according to the fourth aspect of the present disclosure.

Through the whole document, the term "subject" may include, without limitation, mammals including mice, livestock and humans, and farmed fish which develop or are at risk of developing inflammation, an inflammatory disease or asthma.

In an embodiment of the present disclosure, the subject may be other than a human.

In an embodiment of the present disclosure, the pharmaceutical composition may be administered singly or multiply in a pharmaceutically effective amount. In this case, the composition may be formulated and administered in the form of a solution, powder, aerosol, injection, infusion (Ringer solution), capsule, pill, tablet, suppository or patch.

The pharmaceutical composition for preventing or treating inflammation, an inflammatory disease or asthma of the present disclosure may be administered via any route as long as the route allows the pharmaceutical composition to reach a target tissue.

The pharmaceutical composition of the present disclosure may be administered via, but not particularly limited to, intraperitoneal administration, intravenous administration, intramuscular administration, subcutaneous administration, intradermal administration, transdermal patch administration, oral administration, intranasal administration, intrapulmonary administration, rectal administration, etc. depending on the purpose. However, when the pharmaceutical composition is administered via oral administration, it can be administered in an unformulated form, and since the strain of *Lactobacillus sakei* HEM224 can be denatured or degraded by gastric acid, the composition for oral administration may be coated with an active drug, formulated to be protected from degradation in the stomach, or formulated in the form or an oral patch. Also, the composition may be administered by any device capable of delivering an active ingredient to a target cell.

MODE FOR CARRYING OUT THE INVENTION

Hereinafter, the present disclosure will be explained in more detail with reference to Examples. However, the following Examples are illustrative only for better understanding of the present disclosure but do not limit the present disclosure.

EXAMPLES

Example 1: Check of Anti-Inflammatory and Asthma Treatment Effect of *Lactobacillus sakei* HEM224 (In Vitro)

To check an anti-inflammatory effect and an asthma treatment and prevention effect of a novel strain, *Lactobacillus sakei* HEM224 (Depository Institution: Korean Collection for Type Cultures at Korean Research Institute of Bioscience & Biotechnology, Accession Number: KCTC14065BP and Date of Deposit: Dec. 10, 2019), of the present disclosure at the cell level, a test was conducted as described below.

Specifically, RAW 264.7 cells (murine macrophage cell line) were incubated in DMEM medium containing 10% FBS at 37° C. with 10% $CO_2$, and maintained in a 12-well plate at $1 \times 10^5$ cells/well for 48 hours. Cells in serum-free DMEM were co-incubated with probiotics (HEM224, HEM792, HEM382) as test groups at a concentration of $1 \times 10^6$ CFU/well for 16 hours under the conditions of 5% $CO_2$ and 37° C. The test group strains HEM382, HEM792 and HEM224 are *Lactobacillus sakei* HEM224, *Lactobacillus fermentum* HEM792 and *Lactobacillus curvatus* HEM382, respectively. The incubated cells were washed twice with PBS (phosphate-buffered saline), and RNA was extracted from the co-incubated cells by using TRIzol (Invitrogen). After extraction, the mRNA expression level of IL-10 was measured by using qRT-PCR (Quantitative Real-time PCR) to measure the expression level of a cytokine related to T-reg cells (CTRL group was a non-treated control group).

As a result, it was confirmed that the mRNA expression level of IL-10, which is an anti-inflammatory substance, in RAW 264.7 cells (murine macrophage cell line), which are immune cells of mice, is statistically significantly higher in the test groups (HEM224, HEM 792, HEM 382) than in the control group (FIG. 1). Thus, it can be seen that the strains HEM224, HEM 792, and HEM 382 when co-incubated with immune cells, increase the mRNA expression level of IL-10, which is an anti-inflammatory substance or asthma inhibitory substance, in the immune cells.

Also, for comparison of the mRNA expression level of IL-10 in RAW 264.7 cells between each test group and the control group CTRL, a statistical significance of each of the control group and test groups was checked by T-test (*(P-value<0.05),  (P-value<0.01), * (P-value<0.001) in the bar graph).

Based on the above results, it can be seen that the strain HEM224 of the present disclosure can improve the activity or expression level of IL-10, which is an anti-inflammatory factor, and has an anti-inflammatory effect and an effect of treating or alleviating allergy or asthma.

Example 2: Check of Anti-Inflammatory and Asthma Treatment Effect of *Lactobacillus sakei* HEM224 (In Vivo)

To check an anti-inflammatory effect and an asthma treatment and prevention effect of a novel strain, *Lactobacillus sakei* HEM224, of the present disclosure at the animal level, a test was conducted as described below.

Figure 2:
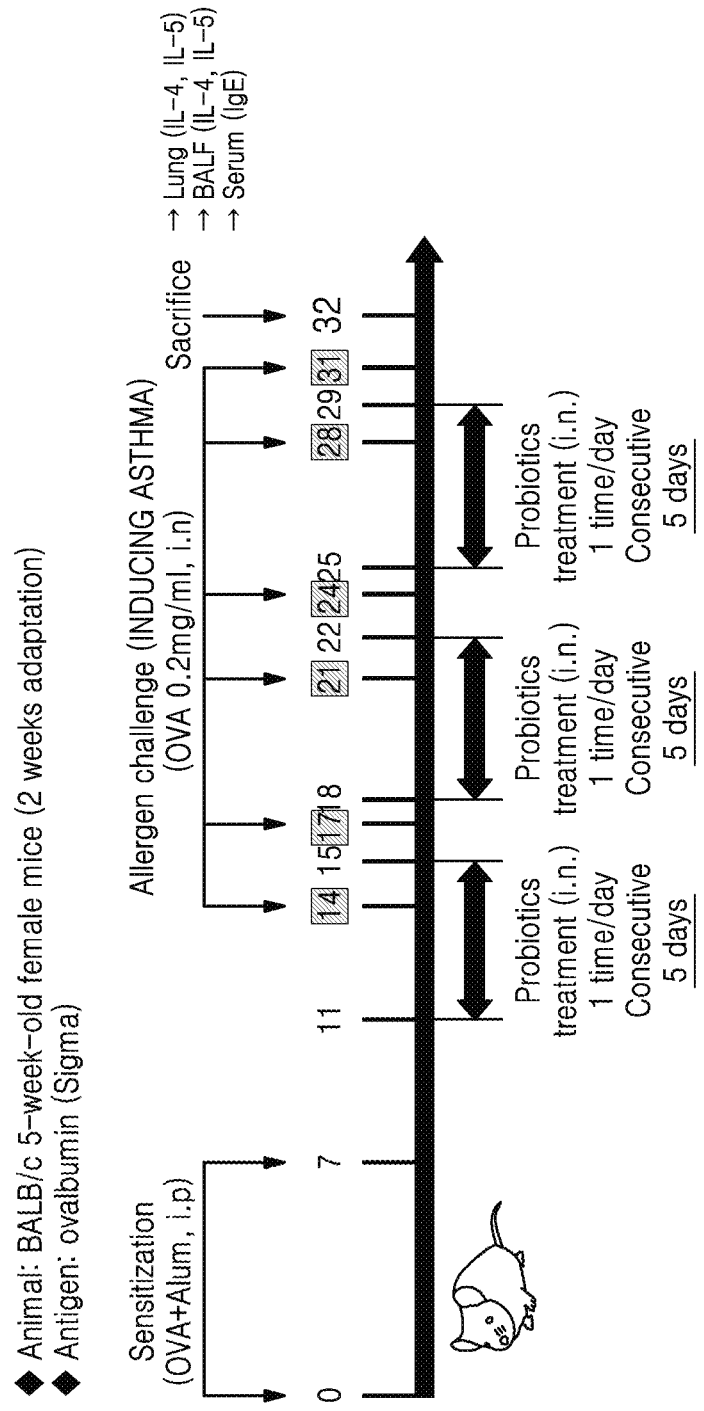
FIG. 2 is a diagram showing an experimental design for confirming the inflammation suppression effect of the novel strain of the present disclosure in a mouse asthma model.

Specifically, 5-week-old female BALB/c mice were prepared, acclimatized to the environment for 2 weeks, and sensitized for 7 days by intraperitoneal (i.p) injection of antigen and adjuvant. In this case, ovalbumin (Sigma) was used as the antigen and aluminum hydroxide was used as the adjuvant. Then, each probiotic (HEM382, HEM792, HEM224) was intranasally injected once daily from day 11 to day 15, from day 18 to day 22 and from day 25 to day 29 of the test, and intranasally injected with ovalbumin (0.2 mg/ml) on day 14, day 17, day 21, day 24, day 28 and day 31 of the test to induce asthma. On day 32 of the test, the lung tissue, bronchoalveolar lavage fluid (BALF) and serum (Serum) were obtained from the mice to analyze the mRNA expression levels or concentrations of IL-4, IL-5 and IgE (FIG. 2).

Example 2-1: Check of Expression Level of IL-4 and IL-5 in Lung Tissue

To check the expression levels of IL-4 and IL-5 from the obtained lung tissue, a test was conducted as described below.

Specifically, the obtained lung tissue was homogenized with TRIzol (700 ul), incubated for 5 minutes at room temperature, lysed by adding 140 ul of chloroform, and incubated for 3 minutes, followed by centrifugation at 12,000 g for 15 minutes at 4° C. to obtain an aqueous phase. 350 ul of isopropanol was added to the obtained aqueous phase, followed by incubation for 10 minutes and centrifugation at 12,000 g for 10 minutes at 4° C. Then, the supernatant was discarded and the pellet was mixed with 700 ul of 75% ethanol (EtOH). The obtained sample was briefly vortexed, and the supernatant obtained by centrifugation at 12,000 g for 5 minutes at 4° C. was discarded and the remaining pellet was dried and mixed with nuclease-free water. Then, RNA yield was measured using absorbance at 260 nm and 280 nm.

Then, to synthesize cDNA from the obtained RNA, the RNA solution was diluted with nuclease-free water to a concentration of 2000 ng/ul (the total volume of the RNA template was set to 9 ul) and then mixed with 1 ul of oligo dT (18 mer) solution to make a total of 10 ul. The sample was heated at 70° C. for 5 minutes and immediately cooled in ice water for 5 minutes or more, and a reverse transcription reaction solution was prepared [10 ul used for each cDNA reaction, composition of the reverse transcription reaction solution: GoScript™ 5× Reaction buffer (4 ul), $MgCl_2$ (2.4 ul), PCR Nucleotide(dNTP) mix (1 ul), GoScript™ Reverse Transcriptase (1 ul), Nuclease-Free water (1.6 ul)]. 15 ul of the reverse transcription reaction solution was mixed with 5 ul of RNA and primer mixture and annealed at 25° C. for 5 minutes, followed by extension reaction at 42° C. for 1 hour to synthesize cDNA.

Thereafter, to check the mRNA expression levels of IL-4 and IL-5 in the synthesized cDNA, a qRT-PCR preparation solution was prepared [composition of the preparation solution: Takara TB Green™ RT-PCR buffer (10 ul), Target primer solution (100 pmol, F+R) (2 ul), ROX reference dye (0.4 ul), Nuclease-Free water (2.6 ul)], a cDNA solution (5 ul) was mixed with the preparation solution (15 ul), and qRT-PCR was performed.

Figure 3:
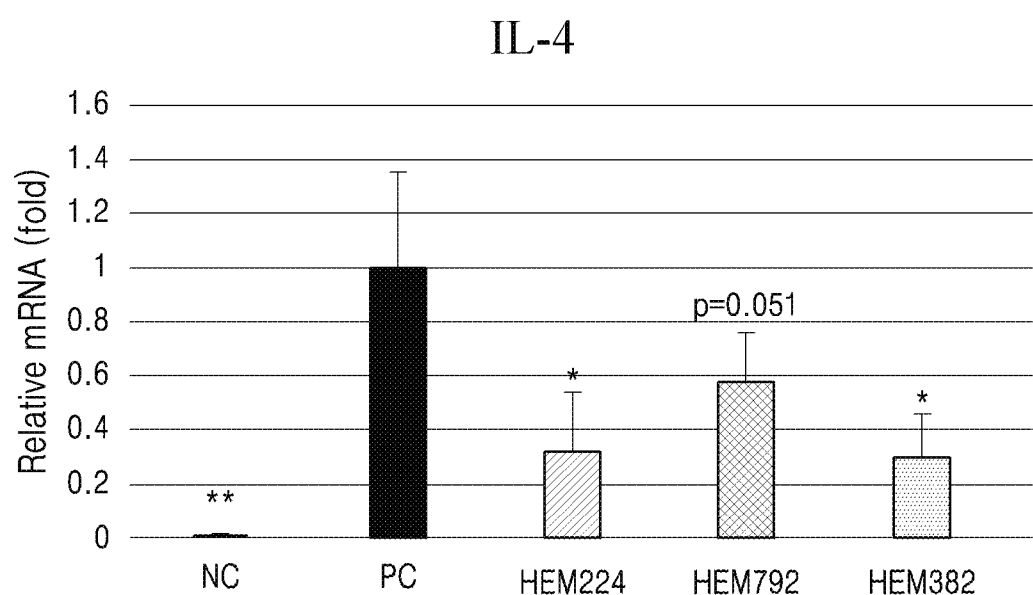
FIG. 3 is a diagram confirming that the novel strain of the present disclosure has a suppressive effect of the production of IL-4 in the lung tissue.

As a result of the test, it can be seen that the mRNA expression level of IL-4, which is a pro-inflammatory substance, in the lung tissue is statistically significantly lower in the test groups treated with HEM224 and HEM382 than in a positive control group PC (a control group in which inflammation or asthma was induced by treatment with an antigen). Also, it can be seen that even the test group treated with HEM 792 has a P-value of 0.051 and decreases the expression level of IL-4 close to statistical significance (FIG. 3).

Figure 4:
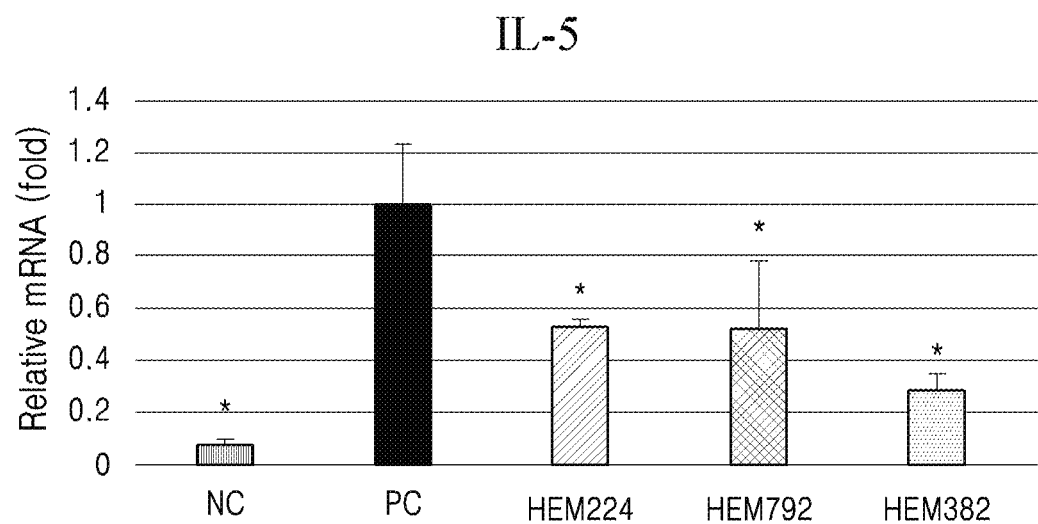
FIG. 4 is a diagram confirming that the novel strain of the present disclosure has a suppressive effect of the production of IL-5 in the lung tissue.

Further, it can be seen that the mRNA expression level of IL-5, which is another pro-inflammatory substance, is statistically significantly lower in the test groups treated with HEM224, HEM792 and HEM382 than in the positive control group (FIG. 4).

(For comparison of the mRNA expression level of IL-4 or IL-5 between each test group and the positive control group PC, a statistical significance of each of PC and the test groups was checked by T-test and shown by * (P-value<0.05),  (P-value<0.01) and * (P-value<0.001) in the bar graph, and each P-value and significance are shown in the table.)

Based on the test results, it can be seen that the strain HEM224 of the present disclosure decreases the mRNA expression levels of IL-4 and IL-5 which are known to induce inflammation in the lung tissue and cause asthma. Therefore, it can be seen that it is possible to inhibit an inflammatory response and treat, prevent or alleviate asthma by using the strain.

Example 2-2: Check of Expression Level of IL-4 and IL-5 in Bronchoalveolar Lavage Fluid To check the expression levels of IL-4 and IL-5 from the obtained bronchoalveolar lavage fluid (BALF), a test was conducted as described below.

Specifically, to check the expression levels of IL-4 and IL-5 by ELISA test method, first, each microwell was coated with 40 μL of capture antibody diluted with a coating buffer, and a test plate was sealed and then incubated at 4° C. overnight. Then, the solution was removed from each well and washed 3 times with 120 ul of wash buffer per well. Thereafter, the test plate was blocked with 80 ul of assay diluent per well and incubated for 1 hour at room temperature. The solution was removed from each well and washed 3 times with 120 ul of wash buffer per well, and standard dilution and sample dilution were prepared by diluting two-fold with assay diluent (concentration gradient: IL-4 test: 500 pg/mL to 7.8 pg/mL, IL-5 test: 1000 pg/mL to 15.6 pg/mL). Then, 40 ul of each of standard, sample and control was pipetted into each well. Thereafter, the test plate was sealed and incubated for 2 hours at room temperature. Then, the solution was removed from each well and washed 3 times with 120 ul of wash buffer per well. 40 ul of each of detection antibody, which is a working detector, and streptavidin-HRP reagent was added into each well. Then, the test plate was sealed and incubated for 1 hour at room temperature. Thereafter, the solution was removed from each well and washed 7 times with 120 ul of wash buffer per well. Then, 40 ul of substrate solution was added into each well and incubated for 30 minutes in a dark place at room temperature, and 20 ul of stop solution was added into each well. The absorbance at 450 nm was measured in 30 minutes after termination reaction, and when wavelength correction was possible, the absorbance at 570 nm was subtracted from the absorbance at 450 nm.

Figure 5:
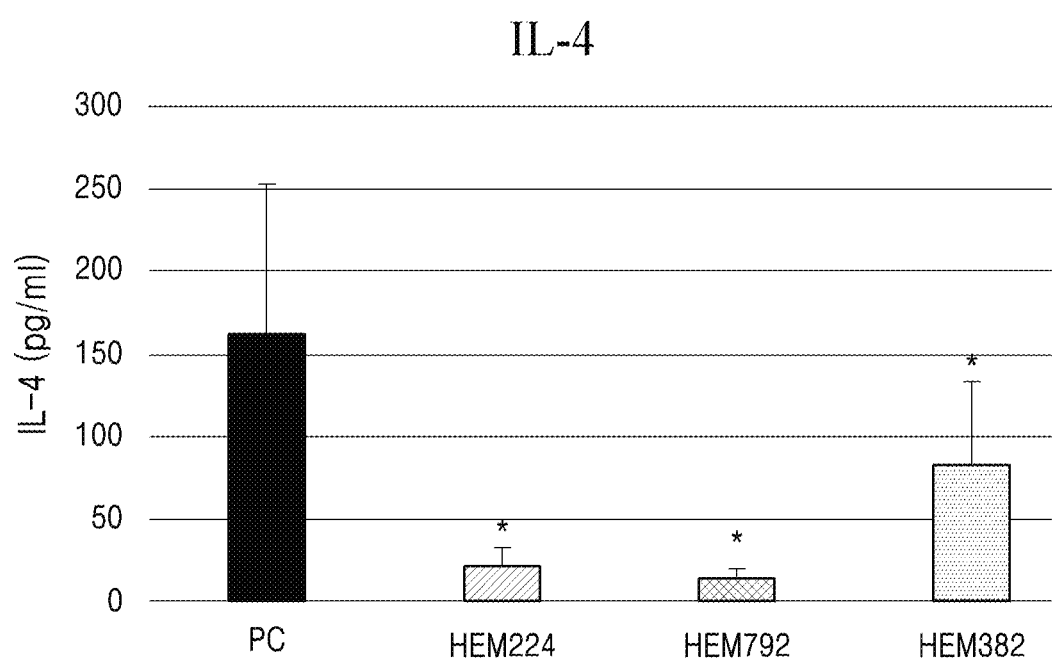
FIG. 5 is a diagram confirming that the novel strain of the present disclosure has a suppressive effect of the production of IL-4 in a bronchoalveolar lavage fluid.

As a result of the test, it can be seen that the concentration of IL-4, which is a pro-inflammatory substance, in the bronchoalveolar lavage fluid is statistically significantly lower in the test groups treated with HEM224, HEM382 and HEM792 than in a positive control group PC (a control group in which inflammation or asthma was induced by treatment with an antigen) (FIG. 5).

Figure 6:
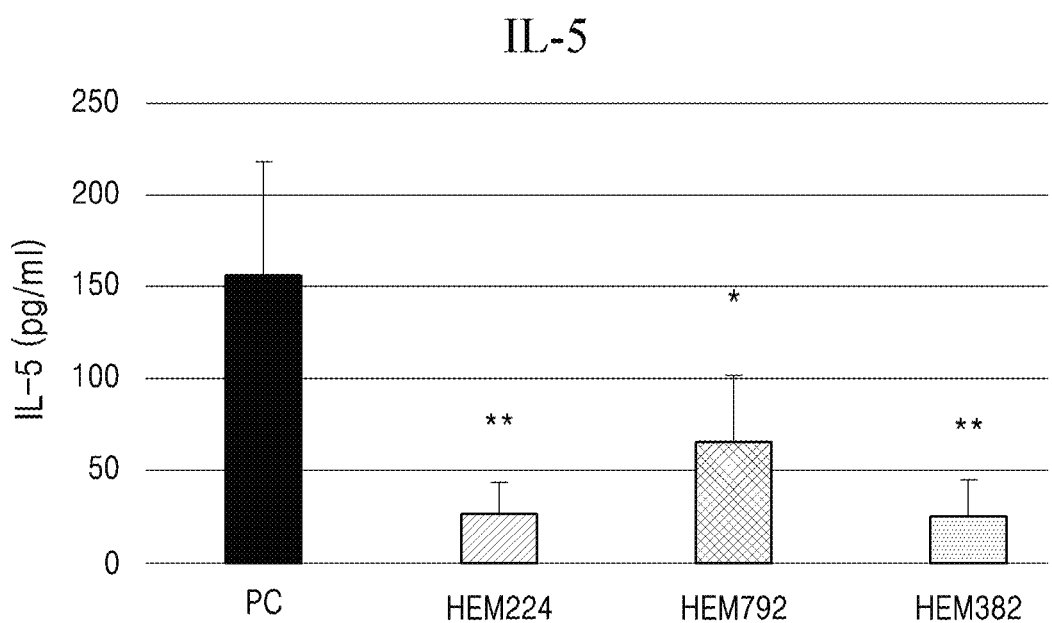
FIG. 6 is a diagram confirming that the novel strain of the present disclosure has a suppressive effect of the production of IL-5 in a bronchoalveolar lavage fluid.

Further, it can be seen that the concentration of IL-5, which is another pro-inflammatory substance, is statistically significantly lower in the test groups treated with HEM224, HEM792 and HEM382 than in the positive control group (FIG. 6).

(For comparison of the concentration of IL-4 or IL-5 between each test group and the positive control group PC, a statistical significance of each of PC and the test groups was checked by T-test and shown by * (P-value<0.05),  (P-value<0.01) and * (P-value<0.001) in the bar graph, and each P-value and significance are shown in the table).

Based on the test results, it can be seen that the strain HEM224 of the present disclosure decreases the concentrations of IL-4 and IL-5 which are known to induce inflammation in the lung and cause asthma. Therefore, it can be seen that it is possible to inhibit an inflammatory response and alleviate asthma by using the strain.

Example 2-3: Check of Expression Level of IgE in Serum

To check the expression level of IgE from the obtained serum, a test was conducted as described below.

Specifically, to check the expression level of IgE by ELISA test method, a capture antibody was diluted with a coating buffer A preparation one day before. Then, 40 ul of the capture antibody solution was added into each well, and a test plate was sealed and incubated overnight for 16 to 18 hours at a temperature between 2° C. and 8° C. and washed 4 times with 120 ul of wash buffer per well. The remaining buffer was removed. Thereafter, to reduce noise (background) and suppress non-specific binding, 80 ul of assay diluent A was added into each well, and the test plate was sealed and then shaken at 300 rpm for 30 minutes at room temperature by using a plate shaker. A serum sample was diluted two-fold with the assay diluent A and standard to 1/10,000 (concentration gradient: 10 ng/mL to 0.156 ng/mL). The plate was washed 4 times with wash buffer and 40 ul of each of standard or sample was added into each well. Thereafter, the plate was sealed and incubated with shaking for 2 hours at room temperature and then washed 4 times with wash buffer. Then, 40 ul of a detection antibody solution was added into each well, and the plate was sealed and incubated with shaking for 1 hour at room temperature and then washed 4 times with wash buffer. 40 ul of Avidin-HRP solution was added into each well, and the plate was sealed and incubated with shaking for 1 hour at room temperature and then washed 5 times with wash buffer. 40 ul of freshly made TMB substrate solution was added into each well and incubated for 20 minutes in a dark place, and 40 ul of stop solution was added into each well. Thereafter, the absorbance at 450 nm was measured in 15 minutes, and when the measuring instrument could measure the absorbance at 570 nm, the value obtained by subtracting the absorbance at 570 nm from the absorbance at 450 nm was used.

Figure 7:
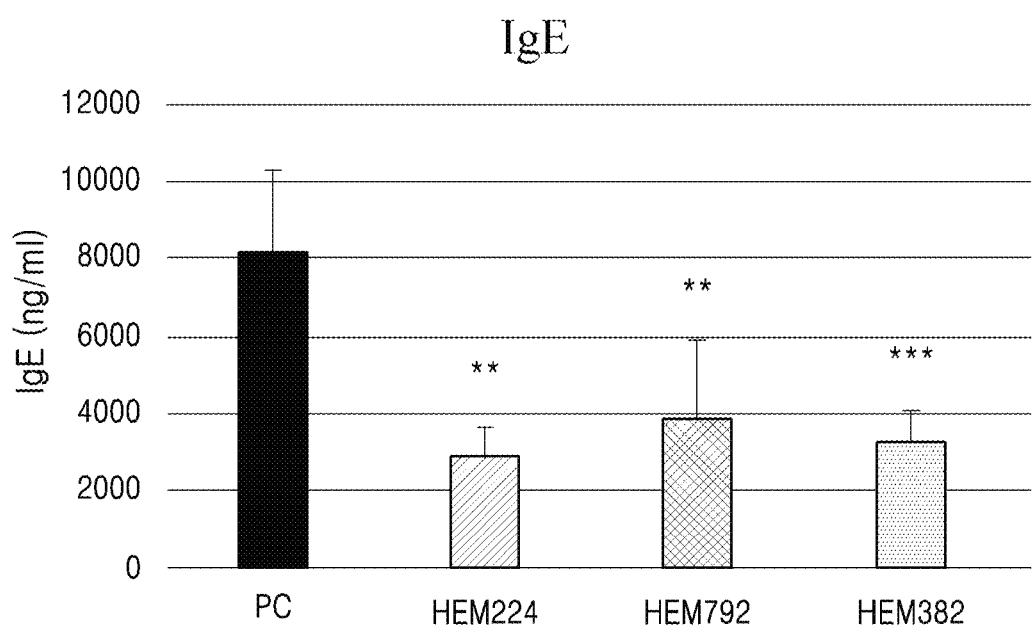
FIG. 7 is a diagram confirming that the novel strain of the present disclosure has a suppressive effect of the production of IgE in the serum.

As a result of the test, it can be seen that the concentration of IgE, which is a pro-inflammatory substance, in the serum is statistically significantly lower in the test groups treated with HEM224, HEM382 and HEM792 than in a positive control group PC (a control group in which inflammation or asthma was induced by treatment with an antigen) (FIG. 7).

(For comparison of the concentration of IgE between each test group and the positive control group PC, a statistical significance of each of PC and the test groups was checked by T-test and shown by * (P-value<0.05),  (P-value<0.01) and * (P-value<0.001) in the bar graph, and each P-value and significance are shown in the table.)

Based on the test results, it can be seen that the strain HEM224 of the present disclosure decreases the concentration of IgE which is known to induce inflammation and cause asthma. Therefore, it can be seen that it is possible to inhibit an inflammatory response and alleviate asthma by using the strain.

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

Accession Number

Depository Institution: Korean Research Institute of Bioscience & Biotechnology
Accession Number: KCTC14065BP
Date of Deposit: Dec. 10, 2019

We claim:

1. A food composition for alleviating or preventing inflammation or asthma, comprising a strain of *Lactobacillus sakei* HEM224 deposited with the Korean Collection for Type Cultures under Accession No. KCTC14065BP, or a cultured product thereof, as an active ingredient, wherein the food composition is selected from sausage, bread, chocolate, candy, cookie, pizza, noodle, gum, ice cream, and beverage, and wherein the strain suppresses the production of IL-4 and IL-5.

2. A pharmaceutical composition for treating or preventing inflammation or asthma, comprising a suspension, a tablet, or vitamin complexes comprising a strain of *Lactobacillus sakei* HEM224 deposited with the Korean Collection for Type Cultures under Accession No. KCTC14065BP or a cultured product thereof as an active ingredient, wherein the strain suppresses the production of IL-4 and IL-5.

3. A method for treating an inflammatory disease including a step of administering the pharmaceutical composition of claim 2 to suppress the production of IL-4 and/or IL-5.

4. The method of claim 3, wherein the inflammatory disease includes at least one selected from the group consisting of asthma, allergic and non-allergic rhinitis, chronic and acute rhinitis, dermatitis, atopic dermatitis and sinusitis.

* * * * *